US012766135B2

(12) United States Patent
Brown

(10) Patent No.: US 12,766,135 B2

(45) Date of Patent: Oct. 20, 2026

(54) TREATMENT OF PLEXIFORM NEUROFIBROMA WITH NITROXOLINE

(71) Applicant: HEALX LTD, Cambridge (GB)

(72) Inventor: David Brown, Cambridge (GB)

(73) Assignee: HEALX LTD, Cambridge (GB)

( * ) Notice: Subject to any disclaimer, the term of this patent is extended or adjusted under 35 U.S.C. 154(b) by 302 days.

(21) Appl. No.: 18/710,477

(22) PCT Filed: Nov. 18, 2022

(86) PCT No.: PCT/GB2022/052933

§ 371 (c)(1), (2) Date: May 15, 2024

(87) PCT Pub. No.: WO2023/089328

PCT Pub. Date: May 25, 2023

(65) Prior Publication Data

US 2025/0000852 A1 Jan. 2, 2025

(30) Foreign Application Priority Data

Nov. 19, 2021 (GB) ..................................... 2116743

(51) Int. Cl.

*A61K 31/47* (2006.01)
*A61K 31/4184* (2006.01)
*A61P 35/00* (2006.01)

(52) U.S. Cl.

CPC .......... *A61K 31/47* (2013.01); *A61K 31/4184* (2013.01); *A61P 35/00* (2018.01)

(58) Field of Classification Search

CPC ...................................................... A61K 31/47
USPC .......................................................... 514/311
See application file for complete search history.

(56) References Cited

FOREIGN PATENT DOCUMENTS

| | | |
|---|---|---|
| WO | WO 2010/042163 | 4/2010 |
| WO | WO 2018/071797 | 4/2018 |
| WO | WO 2020/106304 | 5/2020 |
| WO | WO 2022/258972 | 12/2022 |
| WO | WO 2013/067423 | 5/2023 |

OTHER PUBLICATIONS

Jiang et al. "Nitroxoline (8-hydroxy-5-nitroquinoline) is more a potent anti-cancer agent than clioquinol (5-chloro-7-iodo-8-quinoline)," Cancer Letters, 2011, vol. 312, pp. 11-17.
"MetAP2, a New Therapeutic Target in the NF1 Pathway," Cancer Biology & Therapy, 2005, vol. 4, No. 12, p. 1303.
Burks et al. "Ketotifen Modulates Mast Cell Chemotaxis to Kit-Ligand, but Does Not Impact Mast Cell Numbers, Degranulation, or Tumor Behavior in Neurofibromas of Nf1-Deficient Mice," Molecular Cancer Therapeutics, Dec. 2019, vol. 18, No. 12, pp. 2321-2330.
Cannon et al. "Selumetinib trial targeting cutaneous neurofibromas: preliminary findings and lessons learned," Response Evaluation in Neurofibromatosis Schwannomatosis, 23 pages [online] [Available from: ccrod.cancer.gov/confluence/download/attachments/141000929/5%20-%20WinterREINS_cNFTrial_FINAL_redacted.pdf?version=1&modificationDate=1582049783343 &api=v2] [accessed Nov. 8, 2021].
Kemp "Koselugo (selumetinib) approved in US for paediatric patients with neurofibromatosis type 1 plexiform neurofibromas," AstraZeneca, Apr. 13, 2020, 5 pages [online] [available from: www.astrazeneca.com/media-centre/press-releases/2020/koselugo-selumetinib-approved-in-us-for-paediatric-patients-with-neurofibromatosis-type-1-plexiform-neurofibromas.html] [accessed Nov. 8, 2021].
Killock "Selumetinib benefits children with inoperable plexiform neurofibromas," Nature Reviews Clinical Oncology, Mar. 2020, vol. 17, p. 273.
Kumari et al. "Nitroxoline Exhibit Anticancer Activity Inducing Apoptosis in a Temozolomide-Resistant Glioblastoma," Neuro-Oncology, Nov. 2017, vol. 19, No. Suppl. 6, p. vi59.
Lazovic "Nitroxoline induces apoptosis and slows glioma growth in vivo," Proceedings of the International Society for Magnetic Resonance in Medicine, Apr. 2014, vol. 22, Abstract 1135.
Lazovic et al. "Nitroxoline induces apoptosis and slows glioma growth in vivo," Neuro-Oncology, 2015, vol. 17, No. 1, pp. 53-62.
Mitrovic et al. "Nitroxoline: repurposing its antimicrobial to antitumor application," Acta Biochimica Polonica, Dec. 2019, vol. 66, No. Apr. 2019, pp. 521-531.
Mukhopadhyay et al. "Selumetinib: the first ever approved drug for neurofibromatosis-1 related inoperable plexiform neurofibroma," Current Medical Research and Opinion, 2021, vol. 37, No. 5, pp. 789-794.
Radomska et al. "Cellular Origin, Tumor Progression, and Pathogenic Mechanisms of Cutaneous Neurofibromas Revealed by Mice with Nf1 Knockout in Boundary Cap Cells," Cancer Discovery, Jan. 2019, vol. 9, No. 1, pp. 130-147.
Verma et al. "Considerations for development of therapies for cutaneous neurofibroma," Neurology, Jul. 2018, vol. 91, No. 2 Supplement 1, pp. S21-S30.
International Search Report and Written Opinion for International (PCT) Patent Application No. PCT/GB2022/052933, dated Feb. 28, 2023, 14 pages.
International Preliminary Report on Patentability for International (PCT) Patent Application No. PCT/GB2022/052933, dated May 2, 2024, 9 pages.

(Continued)

*Primary Examiner* — Douglas M Willis
(74) *Attorney, Agent, or Firm* — Sheridan Ross P.C.

(57) ABSTRACT

The present invention relates to a composition comprising nitroxoline, or a pharmaceutically acceptable salt thereof, for use in the treatment or prevention of a plexiform neurofibroma.

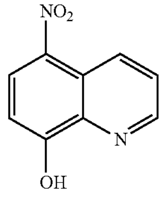

Nitroxoline

17 Claims, 2 Drawing Sheets

(56) References Cited

OTHER PUBLICATIONS

Dasgupta et al. "Cerebrospinal Fluid Proteomic Analysis Reveals Dysregulation of Methionine Aminopeptidase-2 Expression in Human and Mouse Neurofibromatosis 1-Associated Glioma," Cancer Research, Nov. 2005, vol. 65, No. 21, pp. 9843-9850.
Jia et al. "Activated androgen receptor accelerates angiogenesis in cutaneous neurofibroma by regulating VEGFA transcription," International Journal of Oncology, May 2019, vol. 55, pp. 157-166.
Markham et al. "Selumetinib: First Approval," Drugs, 2020, vol. 80, pp. 931-937.
Shim et al. "Effect of Nitroxoline on Angiogenesis and Growth of Human Bladder Cancer," JNCI: Journal of the National Cancer Institute, Nov. 2010, vol. 102, No. 24, pp. 1855-1873.

TREATMENT OF PLEXIFORM NEUROFIBROMA WITH NITROXOLINE

CROSS REFERENCE TO RELATED APPLICATIONS

This application is a national stage application under 35 U.S.C. § 371 and claims the benefit of PCT Application No. PCT/GB2022/052933 having an international filing date of 18 Nov. 2022, which designated the United States, which PCT application claimed the benefit of Great Britain Patent Application No. 2116743.2, filed 19 Nov. 2021, the disclosures of each of which are incorporated herein by reference in their entireties, for all purposes.

FIELD OF THE INVENTION

This invention relates to new uses of nitroxoline.

BACKGROUND OF THE INVENTION

A neurofibroma is a benign nerve-sheath tumour in the peripheral nervous system. In 90% of cases, they are found as stand-alone tumours, while the remainder are found in persons with neurofibromatosis type I (NF1), an autosomal-dominant genetically inherited disease. Neurofibromas can result in a range of symptoms from physical disfiguration and pain to cognitive disability and can transform into malignant tumours.

Plexiform neurofibromas arise during early development from nerves in the skin, or from more internal nerve bundles such as cranial nerves or proximal large peripheral nerve sheaths. Plexiform neurofibromas are composed of Schwann cells (SC), fibroblasts, degranulating mast cells, and vascular cells (Hirota S et al., *Arch Pathol Lab Med.* 1993; 117 (10): 996-9). Plexiform neurofibromas can expand progressively and constitute a lifelong source of morbidity and mortality, with a 10-15% lifetime incidence of transformation to malignant peripheral nerve sheath tumor.

NF1 is caused by germline mutations of the NF1 tumor suppressor gene, which encodes the protein neurofibromin. Neurofibromin functions as a GTPase-activating (GAP) protein and inactivates the intracellular signal transduction protein Ras by converting the active GTP-bound form into its inactive GDP-bound form. This in turn leads to the downregulation of Ras activity. Loss of neurofibromin activity increases Ras activity, which in turn promotes the transcription of a number of genes required for cell growth and proliferation. Plexiform neurofibromas appear in approximately 15% to 40% of patients with NF1.

Internal plexiform neurofibromas are very difficult to remove completely by surgery because they extend through multiple layers of tissue and the attempt would damage healthy tissue or organs. Plexiform neurofibroma can cause disfigurement, neurological, and other clinical deficits including having the potential to cause severe clinical complications if they occur in certain areas.

There have also been considerable efforts to identify pharmacological targets to treat plexiform neurofibromas. In particular plexiform neurofibromas have been a frequent target of repurposing efforts as well as repositioning of drugs in development. Many different standards and methods have been applied to this task. In many cases, repurposing candidates have been identified based primarily on clinical pattern matching, while in others basic disease mechanisms have been studied extensively to identify therapeutic targets, followed by thorough preclinical validation.

At present, surgery remains the primary treatment option. However, removal is difficult because they can be large and cross tissue boundaries. In 2020, the FDA has approved the MEK inhibitor Koselugo (selumetinib) for the treatment of paediatric patients two years of age and older with NF1 who have symptomatic, inoperable plexiform neurofibromas. However, not all patients respond to the treatment and tumors only shrink partially. Selumetinib is a selective inhibitor of mitogen-activated protein kinase kinase (MAPK kinase, MEK, MAP2K, and MAPKK) and has the systemic name 6-(4-bromo-2-chloroanilino)-7-fluoro-N-(2-hydroxyethoxy)-3-methylbenzimidazole-5-carboxamide.

Overall, efforts to treat plexiform neurofibromas have led to some exciting possibilities, but no definitive successes, despite much effort. This has highlighted the need for new therapies.

Nitroxoline is used in humans as an antibiotic, it is not widely used but has been on the market since the 1960s. It is used in the treatment or prevention of biofilm infections, such as urinary tract infections. It is particularly effective at disrupting biofilms and it is the metal cation chelation property that is believed to be responsible for this action. Nitroxoline is metabolised in the liver to the corresponding sulphate and glucuronide metabolites. There is evidence that the metabolites both share the antimicrobial activity. It has also been used in anticancer settings via antiproliferative action. Nitroxoline has the systematic name 5-nitroquinolin-8-ol.

SUMMARY OF THE INVENTION

The present invention is a composition comprising nitroxoline, or a pharmaceutically acceptable salt thereof, for use in the treatment or prevention of a plexiform neurofibroma. As will be evident from the in vitro data presented below, nitroxoline is effective in treating and preventing a plexiform neurofibroma.

A first aspect of the invention is a composition comprising nitroxoline, or a pharmaceutically acceptable salt thereof, for use in the treatment or prevention of a plexiform neurofibroma.

A second aspect of the invention is use of nitroxoline, or a pharmaceutically acceptable salt thereof, for the manufacture of a medicament for use in the treatment or prevention of a plexiform neurofibroma.

A third aspect of the Invention provides a method of treating or preventing a plexiform neurofibroma comprising administering the patient with a composition comprising nitroxoline or a pharmaceutically acceptable salt thereof.

DETAILED DESCRIPTION

Figure 1:
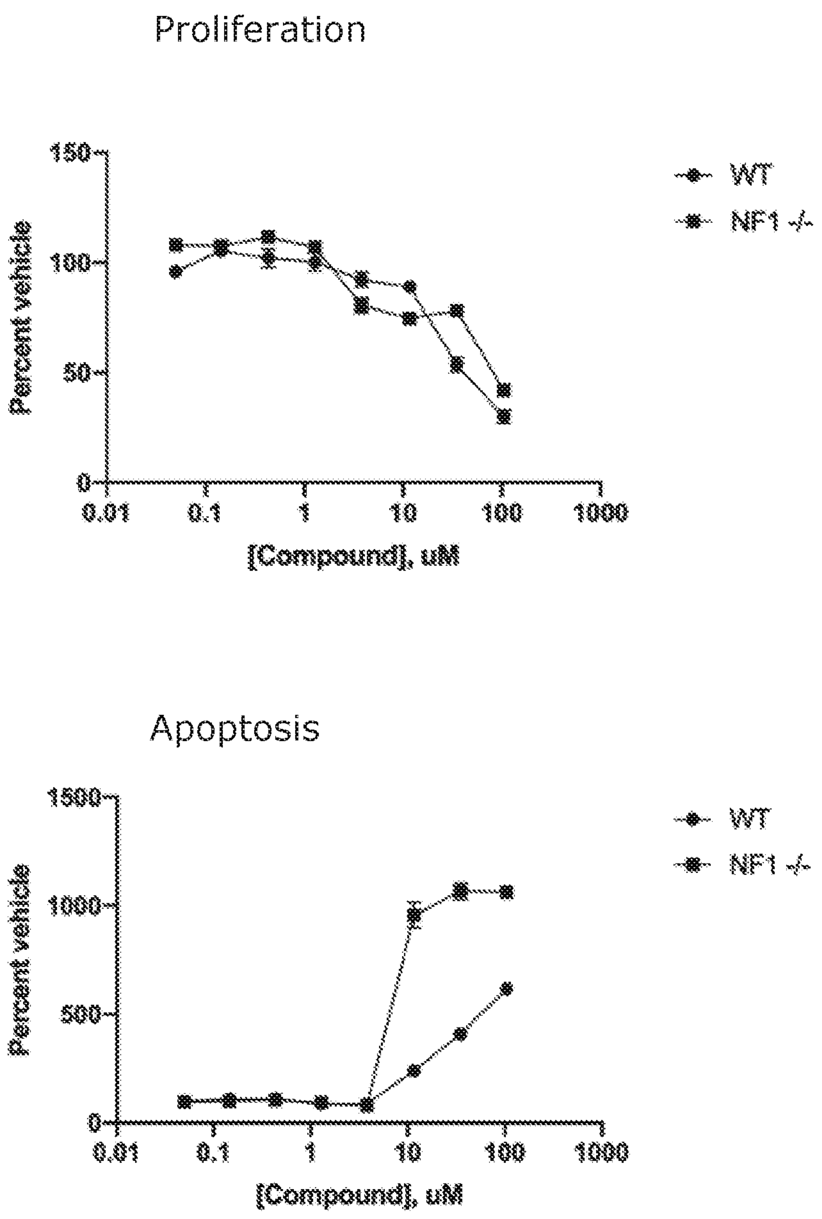
FIG. 1 shows the nitroxoline dose-response in proliferation (top) and apoptosis (bottom) of WT and NF1 deficient Schwann cells in in vitro assays.

Non-myelinating Schwann cells that only express the inactive version of the NF1 gene (a "tumour suppressor gene") leading to a complete loss of expression of functional neurofibromin are the origin of plexiform neurofibromas. The NF1 gene codes for a protein that regulates cell growth. There are two kinds of Schwann cells, myelinating and non-myelinating. While myelinating Schwann cells cover large diameter (>1 micrometer) peripheral nervous system (PNS) axons with myelin, non-myelinating Schwann cells encapsulate small diameter PNS axons with their cytoplasmic processes. In non-mutated non-myelinating Schwann cells, their conglomeration around axons is called a Remak bundle. Whereas, mutated non-myelinating Schwann cells do not form normal Remak bundles. Instead, they fail to properly surround and segregate target axons causing the plexiform neurofibromas. Furthermore, once a non-myelinating Schwann cell has suffered inactivation of its NF1 genes, it begins to proliferate rapidly.

It has been hypothesized that the proliferating non-myelinating Schwann cells secrete chemoattractants that promote the migration of different kinds of cells that are heterozygous for the NF1 gene into the hyperplastic lesions created by the non-myelinating Schwann cells. These cell types include fibroblasts, perineurial cells, endothelial cells, and mast cells. The mast cells then secrete mitogens or survival factors that alter the developing tumor microenvironment and result in neurofibroma formation.

In the present invention, and as demonstrated by the below in vitro data, nitroxoline inhibits cell proliferation and increases apoptosis in NF1 deficient Schwann cells, and is therefore an effective treatment of a plexiform neurofibroma. Preferably, nitroxoline is used for the treatment or prevention of a plexiform neurofibroma, wherein the subject has neurofibromatosis type I.

By the term "treatment" or "treating" as used herein, we refer to therapeutic (curative) treatment, which includes reducing the size of a plexiform neurofibroma. A blood test for protein melanoma inhibitory activity may be used to detect the presence of neurofibromas. By the term "prevention" or "preventing" as used herein, we refer to "prophylactic" treatment, which includes administering the compositions of the invention to a patient that has mutated (e.g. NF1 deficient) non-myelinating Schwann cells but a plexiform neurofibroma has not developed. The mutated (e.g. NF1 deficient) non-myelinating Schwann cells may have begun to proliferate, such as to proliferate rapidly.

"Patient" and "subject" are used interchangeably and refer to the subject that is to be administered the nitroxoline. Preferably the subject is a human. Suitably the subject has neurofibromatosis type I. In one embodiment the patient is a paediatric patient, preferably a paediatric patient 2 years of age and older, preferably the paediatric patient has NF1.

In one embodiment, nitroxoline is used for the treatment or prevention of a plexiform neurofibroma, wherein the patient has had or is going to have surgery to remove some or all of the plexiform neurofibroma. This may be particularly advantageous if the plexiform neurofibroma is large and/or expands across tissue boundaries, so it is difficult to remove it all by surgery and/or a quick removal of at least some of it is desired/beneficial.

The term "surgery" has its normal meaning in the art. Surgery is an invasive technique with the fundamental principle of physical intervention on organs/organ systems/tissues for diagnostic or therapeutic reasons.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

The present invention is directed to a composition comprising nitroxoline, or a pharmaceutically acceptable salt thereof, for use in the treatment or prevention of a plexiform neurofibroma.

In an alternative embodiment, the present invention is directed to a composition comprising nitroxoline, or a pharmaceutically acceptable salt thereof, for use in the treatment or prevention of a plexiform neurofibroma, wherein nitroxoline is the only active agent in the composition. By only active agent it is meant that the composition does not contain other components which may be used in the treatment or prevention of a plexiform neurofibroma. In an alternative embodiment, the composition further comprises a second active agent for treating plexiform neurofibroma, preferably wherein the second active agent is selumetinib, or a pharmaceutically acceptable salt thereof.

In an alternative embodiment, the present invention is directed to a composition comprising nitroxoline, or a pharmaceutically acceptable salt thereof, for use in combination with a second composition comprising selumetinib, or a pharmaceutically acceptable salt thereof, wherein the two compositions are administered to the subject simultaneously, separately or sequentially.

As used herein, "separate" administration means that the drugs are administered as part of the same overall dosage regimen (which could comprise a number of days), but preferably on the same day. As used herein "simultaneously" means that the drugs are to be taken together or formulated as a single composition. As used herein, "sequentially" means that the drugs are administered at about the same time, and preferably within about 1 hour of each other. Preferably, the drugs are administered simultaneously i.e. taken together or formulated as a single composition. Most preferably, they are formulated as a single composition.

The compositions of the invention may contain a pharmaceutically acceptable carrier. By "pharmaceutically acceptable carrier" is meant any diluent or excipient, such as fillers or binders, that is compatible with the other ingredients of the composition, and which is not deleterious to the recipient. The pharmaceutically acceptable carrier can be selected on the basis of the desired route of administration, in accordance with standard pharmaceutical practices.

In the present invention, the composition may be administered in a variety of dosage forms. In one embodiment, the composition may be formulated in a format suitable for oral, rectal, parenteral, intranasal or transdermal administration or administration by inhalation or by suppository.

The composition may be administered orally, for example as tablets, troches, lozenges, aqueous or oily suspensions, dispersible powders or granules. Preferably, the composition is formulated such that it is suitable for oral administration, for example tablets and capsules. Tablets and capsules may be prepared with binding agents, for example, syrup, acacia, gelatin, sorbitol, tragacanth, celluloses or polyvinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats;

emulsifying agents and surfactants such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

The composition may also be administered parenterally, whether subcutaneously, intravenously, intramuscularly, intrasternally, transdermally or by infusion techniques.

The composition may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed.

The present invention also provides an inhalation device containing the composition of the present invention. Typically said device is a metered dose inhaler (MDI), which contains a pharmaceutically acceptable chemical propellant to push the medication out of the inhaler.

The composition may also be administered by intranasal administration. The nasal cavity's highly permeable tissue is very receptive to medication and absorbs it quickly and efficiently. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing the composition according to the present invention.

The composition may also be administered by transdermal administration. For topical delivery, transdermal and transmucosal patches, creams, ointments, jellies, solutions or suspensions may be employed. The present invention therefore also provides a transdermal patch containing the composition.

The composition may also be administered by sublingual administration. The present invention therefore also provides a sub-lingual tablet comprising the composition.

The composition may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In an embodiment of the invention, the composition is administered in an effective amount to treat or prevent a plexiform neurofibroma. An effective dose will be apparent to one skilled in the art, and is dependent on a number of factors including age, sex, weigh, which the medical practitioner will be capable of determining.

In a preferred embodiment, the composition comprises 30 mg to 600 mg, preferably 50 mg to 500 mg, more preferably 100 mg to 400 mg, yet more preferably 150 mg to 350 mg, most preferably 200 mg to 300 mg nitroxoline.

The composition may be administered once a day, twice a day, three times a day or four times a day.

In an embodiment of the invention, the composition is administered at least once a day. Preferably it is administered as a single daily dose. Preferably the single daily dose is 90 mg to 1800 mg, preferably 150 mg to 1500 mg, more preferably 300 mg to 1200 mg, yet more preferably 450 mg to 1050 mg, most preferably 600 mg to 900 mg of nitroxoline.

In an embodiment of the invention, the composition is administered twice daily. Preferably each dose is 45 mg to 900 mg, preferably 75 mg to 750 mg, more preferably 150 mg to 600 mg, yet more preferably 225 mg to 525 mg, most preferably 300 mg to 450 mg of nitroxoline.

In an embodiment of the invention, the composition is administered three times daily. Preferably each dose is 30 mg to 600 mg, preferably 50 mg to 500 mg, more preferably 100 mg to 400 mg, yet more preferably 150 mg to 350 mg, most preferably 200 mg to 300 mg of nitroxoline.

In an embodiment of the invention, the composition is administered four times daily. Preferably each dose is 15 mg to 500 mg, preferably 50 mg to 400 mg, more preferably 100 mg to 300 mg, yet more preferably 125 mg to 225 mg, most preferably 150 mg to 200 mg of nitroxoline.

Preferably, the dosage regime is such that the total daily dosage of nitroxoline does not exceed 1500 mg.

Suitably the dosage of nitroxoline may be between 50 and 250 mg/kg, more preferably between 60 and 200 mg/kg, even more preferably between 80 and 170 mg/kg, such as between 100 and 150 mg/kg.

Suitably the effective dose of nitroxoline results in a concentration of 1 to 150 μM, preferably 10 to 100 μM, more preferably 25 to 50 UM in cells.

Suitably the composition comprising nitroxoline and the second composition comprising the second active agent, preferably selumetinib, are a single daily dose. Suitably the two compositions are administered simultaneously i.e. nitroxoline and selumetinib are taken together. The compositions may also be administered sequentially i.e. at about the same time, and preferably within about 1 hour of each other.

In the embodiments wherein the composition comprises selumetinib or the composition is for use in combination with a second composition comprising selumetinib, suitably the compositions comprising selumetinib comprise between 1 mg and 75 mg of selumetinib, preferably between 5 mg to 50 mg of selumetinib, more preferably between 10 mg to 35 mg of selumetinib, most preferably between 15 mg to 30 mg of selumetinib.

Suitably the effective dose of selumetinib administered to the subject is between 1 $mg/m^2$ and 75 $mg/m^2$ of selumetinib, preferably between 5 $mg/m^2$ to 50 $mg/m^2$ of selumetinib, more preferably between 10 $mg/m^2$ to 35 $mg/m^2$ of selumetinib, most preferably between 15 $mg/m^2$ to 30 $mg/m^2$ of selumetinib.

In order to treat or prevent a plexiform neurofibroma, the composition comprising nitroxoline is used in a chronic dosage regime i.e. chronic, long-term treatment. Suitably the regime lasts for at least one month, suitably at least two months, such as at least three months.

The present invention also relates to a kit comprising: (i) at least one dose of nitroxoline, or a pharmaceutically acceptable salt thereof; and optionally (ii) at least one dose of selumetinib, or a pharmaceutically acceptable salt thereof, for simultaneous, separate or sequential use in the treatment or prevention of a plexiform neurofibroma.

The present invention also relates to use of nitroxoline, or a pharmaceutically acceptable salt thereof, for the manufacture of a medicament for use in the treatment or prevention of a plexiform neurofibroma. This embodiment of the invention may have any of the preferred features described above.

The present invention also relates to a method of treating or preventing a plexiform neurofibroma comprising administering the patient with a composition comprising nitroxoline or a pharmaceutically acceptable salt thereof. This embodiment of the invention may have any of the preferred features described above. The method of administration may be according to any of the routes described above.

For the avoidance of doubt, the present invention also embraces prodrugs which react in vivo to give a compound of the present invention.

EXAMPLE SECTION

Example 1-In Vitro Drug Testing Utilizing WT and NF1 Deficient Schwann Cells In this study the efficacy of nitroxoline was investigated and its ability to reduce cellular proliferation, increase apoptosis, and overall cell viability utilizing immortalized wild-type (WT) and NF1 deficient ($Nf1^{-/-}$) Schwann cells (SCs).

$Nf1^{-/-}$ SCs have increased survival and proliferation in vitro, consistent with the in vivo phenotypes (Kim H A et al., *Mol Cell Biol.* 1997; 17 (2): 862-72). The present studies utilize WT (ipn02.3λ) and $NF1^{-/-}$ (ipNF95.6) immortalized human-derived SC lines. The selectivity of nitroxoline was compared between $NF1^{-/-}$ and WT cells.

Cells were treated with serially diluted nitroxoline starting from 105 UM and incubated for 48 hours. After the incubation period, proliferation, viability, and apoptosis assays were performed as described below:

- Cell proliferation was assessed using the CellTiter-Glo Assay (Promega) which measures ATP consumption. Briefly, WT and $Nf1^{-/-}$ cells were plated in triplicate at a concentration of 10,000 cells/well in 96-well dishes in 100 μl DMEM containing 1% glutamine, 10% FBS, 2% Sodium Bicarbonate and 1% Penicillin/Streptomycin, in a 37° C., 5% $CO_2$ humidified incubator with or without the addition of nitroxoline for 48 hours. Following incubation, 100 μl of CellTiterGlo reagent was added to each well. After 10 minutes, the plates were read using a 96-well microplate luminometer,
- Cellular apoptosis was assessed using the Caspase-Glo 3/7 kit (Promega), Briefly, WT and $Nf1^{-/-}$ cells were plated in triplicate at a concentration of 10,000 cells/well in 96-well dishes in 100 μl DMEM containing 1% glutamine, 10% FBS, 2% Sodium Bicarbonate and 1% Penicillin/Streptomycin, in a 37° C., 5% $CO_2$ humidified incubator with or without the addition of nitroxoline for 48 hours. Following incubation, 100 μl Caspase-Glo 3/7 reagent was added to each well. After 10 minutes, plates were read using a 96 well luminometer and caspase 3/7 activity was measured.

Results

Nitroxoline inhibited cell proliferation and increased apoptosis in a dose-response manner, as seen in FIG. 1. The antiproliferative effect was observed at concentrations greater than 1 μM in WT and $Nf1^{-/-}$ Schwann cells. The induction of apoptosis was evident at concentrations greater than 3 μM in both SCs but the magnitude of the increase was significantly greater in $Nf1^{-/-}$ SC at concentrations greater than 10 μM.

Example 2—In Vivo Drug Testing in Nf1-KO Mice

The aim of this study was to evaluate the effect of nitroxoline in a mouse model of neurofibromatosis type 1, more specifically a model that develops plexiform neurofibromas. This study is the same used by AstraZeneca for the approval of selumetinib for pNF.

Animals

Figure 3:
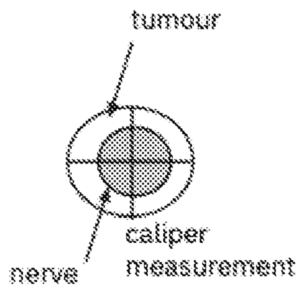
FIG. 3 shows a graphic of the tumour/nerve width and how the caliper measurement is taken.

This study uses the Postn-$Cre^{+}Nf1^{fl/fl}$ mouse model of plexiform neurofibroma. The neurofibromas that arise in these mice faithfully recapitulate human disease (Burks et al. 2019). At 4 months of age when mice (male and female) had established plexiform neurofibromas they were randomised into three treatment groups and administered nitroxoline at 120 mg/kg QD, 120 mg/kg BD or vehicle (10% DMSO in 90% corn oil) via oral gavage. Mice were treated for 12 weeks then sacrificed. Mice were perfused and fixed in 10% neutral buffered formalin, Nerve Volume The whole bodies were decalcified in 5% formic acid, the spinal proximal nerve tree was dissected, and nerve width (including the tumour formed along it) measured via calliper (shown in FIG. 3) across four nerves per mouse. Nerve volume was subsequently calculated using a spheroid calculation: 0.52×(width)2 w length.

Tumour Number

To quantify tumour number, the nerves were processed to paraffin blocks, sectioned, and stained for collagen using Masson's trichrome stain. Tumour number was scored from these slides by a clinician.

Statistical Analysis

Graphs and statistical analysis of data were produced using GraphPad Prism (Ver 9).

Results

Figure 2:
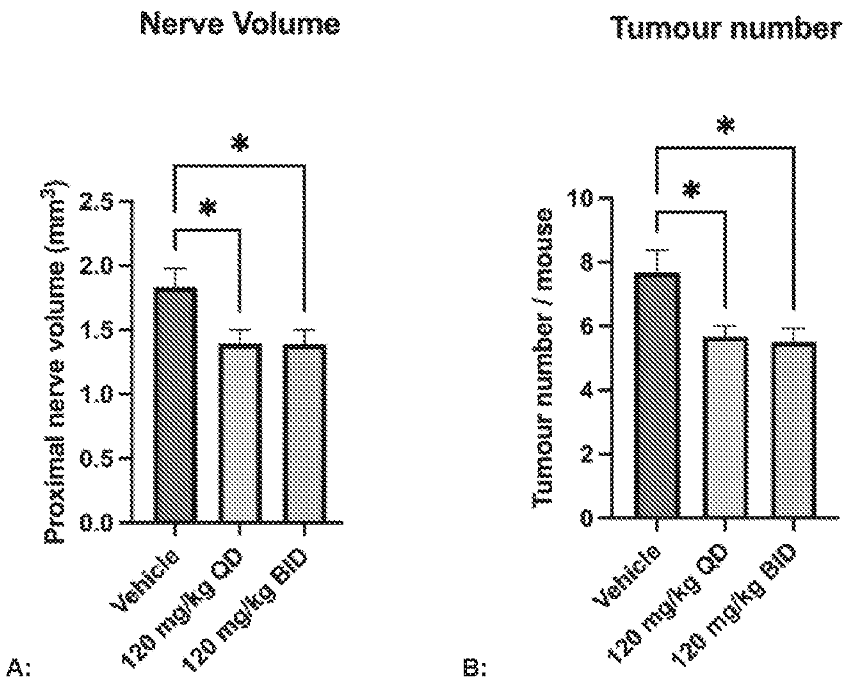
FIG. 2 shows the effect of nitroxoline treatment on proximal nerve volume (A) and tumour number (B) in the Postn-Cre+$Nf1^{fl/fl}$ mouse model of plexiform neurofibroma (n=6, *=p value<0.05 Fisher's LSD test/Dunnett's test).

Mice treated with nitroxoline at both dose schedules (120 mg/kg QD and 120 mg/kg BD) had lower proximal nerve volumes compared to vehicle treated control mice (FIG. 2). Plexiform tumours form along the proximal nerves, therefore a reduction in proximal nerve volume can be interpreted as a reduction in plexiform tumour size. In addition to a reduction in total nerve volume, a reduction in tumour number along the nerves was observed in nitroxoline treated mice compared to vehicle controls (FIG. 2).

CONCLUSIONS

Nitroxoline inhibits cell proliferation and increases apoptosis in vitro in $Nf1^{-/-}$ Schwann cells. In a mouse model of plexiform neurofibroma, nitroxoline treated mice had lower proximal nerve volumes and less tumours compared to vehicle control animals. It is thus expected that nitroxoline will reduce, treat and prevent plexiform neurofibromas.

REFERENCES

Burks C A, Rhodes S D, Bessler W K, Chen S, Smith A, Gehlhausen J R, Hawley E T, Jiang L, Li X, Yuan J, Lu Q, Jacobsen M, Sandusky G E, Jones D R, Clapp D W, Blakeley J O. Ketotifen Modulates Mast Cell Chemotaxis to Kit-Ligand, but Does Not Impact Mast Cell Numbers, Degranulation, or Tumor Behavior in Neurofibromas of Nf1-Deficient Mice. Mol Cancer Ther. 2019 December; 18(12): 2321-2330.

The invention claimed is:

1. A method for treating a plexiform neurofibroma in a subject, wherein the method comprises administering to the subject in need thereof a therapeutically effective amount of a pharmaceutical composition comprising a pharmaceutically acceptable carrier and nitroxoline of the following formula:

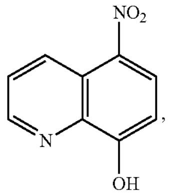 [SMILES: O=[N+]([O-])c1ccc(O)c2ncccc12]

or a pharmaceutically acceptable salt thereof.

2. The method according to claim 1, wherein the subject has neurofibromatosis type I.

3. The method according to claim 1, wherein the subject in need thereof is administered twice daily a single dose of the pharmaceutical composition comprising a pharmaceutically acceptable carrier and nitroxoline, or a pharmaceutically acceptable salt thereof.

4. The method according to claim 3, wherein each single dose of the pharmaceutical composition comprises nitroxoline, or a pharmaceutically acceptable salt thereof, in an amount in the range of 150 mg to 600 mg.

5. The method according to claim 1, wherein the subject in need thereof is administered three times daily a single dose of the pharmaceutical composition comprising a pharmaceutically acceptable carrier and nitroxoline, or a pharmaceutically acceptable salt thereof.

6. The method according to claim 5, wherein each single dose of the pharmaceutical composition comprises nitroxoline, or a pharmaceutically acceptable salt thereof, in an amount in the range of 30 mg to 600 mg.

7. The method according to claim 1, wherein the subject in need thereof is administered four times daily a single dose of the pharmaceutical composition comprising a pharmaceutically acceptable carrier and nitroxoline, or a pharmaceutically acceptable salt thereof.

8. The method according to claim 7, wherein each single dose of the pharmaceutical composition comprises nitroxoline, or a pharmaceutically acceptable salt thereof, in an amount in the range of 15 mg to 500 mg.

9. The method according to claim 1, wherein the subject is a human.

10. The method according to claim 1, wherein the pharmaceutical composition comprises nitroxoline in an amount in the range of 30 mg to 600 mg.

11. The method according to claim 1, wherein nitroxoline, or a pharmaceutically acceptable salt thereof, is the only active agent in the pharmaceutical composition.

12. The method according to claim 1, wherein the pharmaceutical composition is administered intravenously or orally to the subject in need thereof.

13. The method according to claim 1, wherein the pharmaceutical composition is administered parenterally, rectally, sublingually, transdermally, or by inhalation to the subject in need thereof.

14. The method according to claim 1, wherein the pharmaceutical composition further comprises selumetinib, or a pharmaceutically acceptable salt thereof, as an active agent.

15. The method according to claim 14, wherein the pharmaceutical composition comprises selumetinib, or a pharmaceutically acceptable salt thereof, in an amount in the range of 1 mg to 75 mg.

16. The method according to claim 1, wherein the method further comprises:

(a) administering to the subject in need thereof a second pharmaceutical composition comprising a therapeutically effective amount of selumetinib, or a pharmaceutically acceptable salt thereof; and (b) separately, sequentially, or simultaneously administering to the subject in need thereof both pharmaceutical compositions.

17. The method according to claim 16, wherein the therapeutically effective amount of selumetinib, or a pharmaceutically acceptable salt thereof, is in the range of 1 mg to 75 mg.

* * * * *